United States Patent [19]
Langel et al.

[11] Patent Number: 6,025,140
[45] Date of Patent: Feb. 15, 2000

[54] MEMBRANE-PERMEABLE CONSTRUCTS FOR TRANSPORT ACROSS A LIPID MEMBRANE

[75] Inventors: Ulo Langel, Bandhagen, Sweden; Tamas Bartfai, Basel, Switzerland; Margus Pooga; Andres Valkna, both of Tartu, Estonia; Külliki Saar, Lidingo; Mattias Hallbrink, Stockholm, both of Sweden

[73] Assignee: Perseptive Biosystems, Inc., Framingham, Mass.

[21] Appl. No.: 09/116,294

[22] Filed: Jul. 16, 1998

Related U.S. Application Data

[60] Provisional application No. 60/053,678, Jul. 24, 1997.
[51] Int. Cl.$^7$ .............. C07H 21/04; C12Q 1/68; C12N 15/85
[52] U.S. Cl. .............. 435/6; 435/325; 530/323; 536/23.1; 536/24.5
[58] Field of Search ............ 435/6, 325; 536/23.1, 536/24.5; 530/323

[56] References Cited

FOREIGN PATENT DOCUMENTS

| | | |
|---|---|---|
| 0514361 | 5/1992 | European Pat. Off. . |
| WO 90/00168 | 1/1990 | WIPO . |
| WO 91/14696 | 10/1991 | WIPO . |
| WO 93/11784 | 6/1993 | WIPO . |
| WO 94/13325 | 6/1994 | WIPO . |
| WO 96/11205 | 4/1996 | WIPO . |

OTHER PUBLICATIONS

Allinquant et al., Downregulation of Amyloid Precursor Protein Inhibits Neurite Outgrowth In Vitro, *Jnl. of Cell Biol.* 128(5):919–927 (Mar. 1995).

Langel et al., "A galanin–mastoparan chimeric peptide activates the NA$^+$, K$^+$—ATPase and reverses its inhibition by ouabain," *Regulatory Peptides* 62:47–52 (1996).

Troy et al., "Downregulation of Cu/Zn Superoxide Dismutase Leads to Cell Death via the Nitric Oxide–Peroxynitrite Pathway," *Jnl. Neurosci.* 16(1):253–261 (Jan. 1, 1996).

van der Laan, "A Convenient Automated Solid–Phase Synthesis of PNA –(5')–DNA–(3')–PNA Chimera," *Terahedron Letters* 38(13):2249–2252 (1997).

Vinayak et al., "Automated Chemical Synthesis of PNA and PNA–DNA Chimera on a Nucleic Acid Synthesizer," *Nucleosides & Nucleotides* 16(7–9):1653–1656 (1997).

Prochiantz, Alain, "Getting hydrophilic compounds into cells: lessons from homepeptides," *Current Opinion in Neurobiology*, 6:629–634 (1996).

Prochiantz, Alain, "Peptide nucleic acid smugglers," *Nature Biotechnology*, 16:819–820 (Sep. 1998).

Simmons et al, "Synthesis and Membrane Permeability of PNA–Peptide Conjugated," *Bioorganic & Medicinial Chemistry Letters*, 7(23): 3001–3006 (1997).

*Primary Examiner*—John S. Brusca
*Assistant Examiner*—Andrew Wang
*Attorney, Agent, or Firm*—Alex Andrus

[57] ABSTRACT

Constructs of peptides and nucleic acid analogs conjugated together for transport across a lipid membrane and for delivery into interactive contact with intracellular polynucleotides are disclosed. Transport is effected through at least the exterior membrane of a cell, and most likely also through the walls of subcellular structures separated from the cytosol by lipid membranes, including the nucleus, mitochondria, ribosomes, etc. Peptide nucleic acid (PNA) analog sequences conjugated through a labile disulfide bond to transporting peptides, are intracellulary cleaved, and target mRNA (antigene) or dsDNA (antisense).

22 Claims, 8 Drawing Sheets

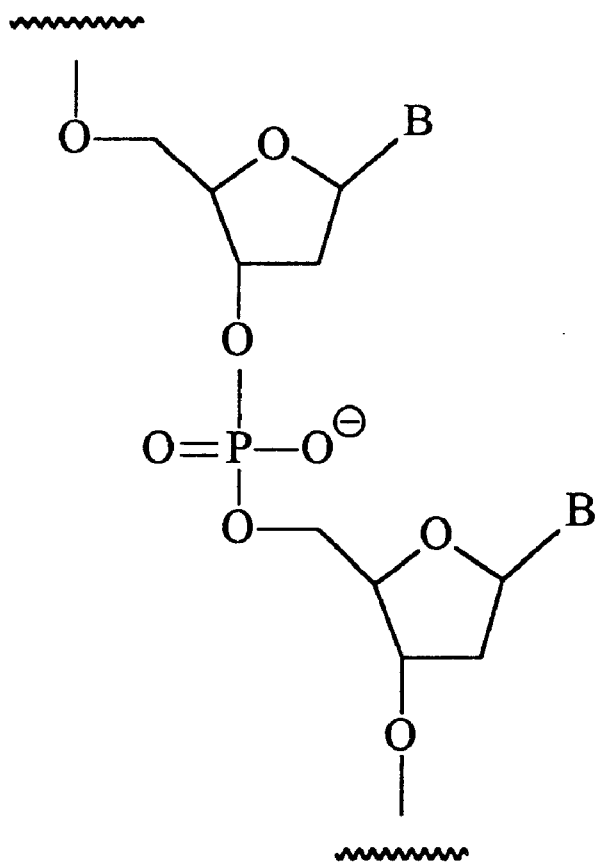 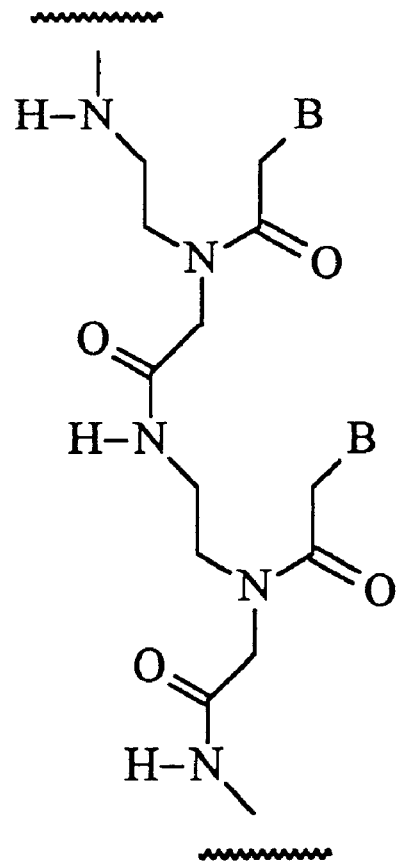
DNA    PNA
Fig. 1

Human galanin receptor biotin-Cys-cPNA (18-32):

biotin-Cys-CCC TCG CTG AGG TTC-amide  1

Cys(Npys)-pAntp(43-58) 2 + biotin-Cys-cPNA (18-32) 1

```
Cys-RQIKIWFQNRRMKWKK-amide
 |
 S
 |
 S
 |
biotin-Cys-CCC TCG CTG AGG TTC-amide
```

Synthesis of cPNA(18-32)-S-S-pAntp(43-58) by coupling human galanin receptor biotin-Cys-cPNA 1 to Cys(Npys)-pAntp(43-58) 2

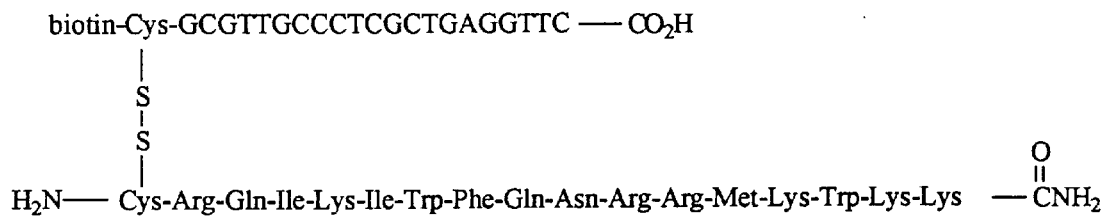
pAntp(43-58)-S-S-(biotinyl PNA21)  A
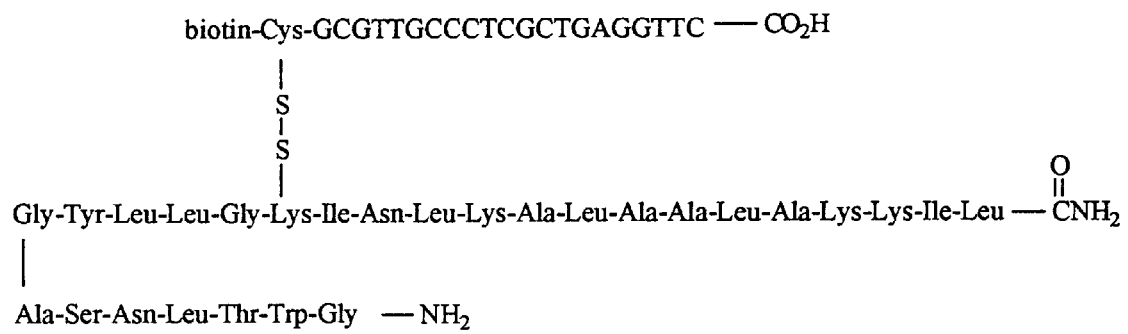
transportan-S-S-(biotinyl PNA21)  B
Fig. 4 pAntp(43-58)-S-S-(biotinyl PNA21)A

| Coding region of human/rat galanin receptor type 1 mRNA: | Construct/Nucleic acid analogs | $EC_{50}$, µM |
|---|---|---|
| 18-38 | cPNA h(18-38)-S-S-pAntp A | 0.33 ± 0.18 |
| | cPNA h(18-38)-S-S-transportan B | 0.20 ± 0.11 |
| | phosphorothioate h(18-38) | 21.5* |
| | phosphodiester h(18-38) | >100 |
| 1-21 | cPNA h(1-21)-S-S-pAntp | 1.9 ± 0.5 |
| | cPNA h(1-21)-S-S | 0.6 ± 0.3 |
| 1-18 | Phosphodiester h(1-18) | >100 |

Controls:

| | | |
|---|---|---|
| 18-38 | scrambled PNA h(18-38)-S-S-pAntp | >100 |
| | scrambled PNA h(18-38)-S-S-transportan | >100 |
| | cPNA r(18-38)-S-S-pAntp A | >10 |
| | cPNA r(18-38)-S-S-transportan B | >10 |
| | cPNA h(18-38) | >100 |
| 1-21 | cPNA r(1-21)-S-S-pAntp | >10 |
| | cPNA r(1-21)-S-S-transportan | >10 |
| carrier peptides | transportan | >100 |
| | pAntp(43-58) | >100 |

* extrapolated value

| | | |
|---|---|---|
| cPNA h(1-21) | ATG GAG CTG GCG GTC GGG AAC amide | (SEQ. ID NO. 13) |
| cPNA h(18-38) | GCG TTG CCC TCG CTG AGG TTC amide | (SEQ. ID NO. 7) |
| PNA h(18-38) scrambled | GGC ATG GCT GCT CTC CGT CTG amide | (SEQ. ID NO. 14) |
| cPNA r(1-21) | ATG GAA CTG GCT CCG GTG AAC amide | (SEQ. ID NO. 15) |
| cPNA r(18-38) | CCA TTC CCT TCA CTG AGG TTC amide | (SEQ. ID NO. 16) |

Fig. 6

SEQUENCE LISTING

```
<160> NUMBER OF SEQ ID NOS: 16

<210> SEQ ID NO 1
<211> LENGTH: 14
<212> TYPE: PRT
<213> ORGANISM: wasp

<400> SEQUENCE: 1

Ile Asn Leu Lys Ala Leu Ala Ala Leu Ala Lys Lys Ile Leu
1               5                   10

<210> SEQ ID NO 2
<211> LENGTH: 12
<212> TYPE: PRT
<213> ORGANISM: wasp

<400> SEQUENCE: 2

Gly Trp Thr Leu Asn Ser Ala Gly Tyr Leu Leu Gly
1               5                   10

<210> SEQ ID NO 3
<211> LENGTH: 27
<212> TYPE: PRT
<213> ORGANISM: k:åsp

<400> SEQUENCE: 3

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 4
<211> LENGTH: 16
<212> TYPE: PRT
<213> ORGANISM: drosphila

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 24
<212> TYPE: DNA
<213> ORGANISM: human galanin receptor mRNA

<400> SEQUENCE: 5
gtcgggaacc tcagcgaggg caac                                          24

<210> SEQ ID NO 6
<211> LENGTH: 21
```

```
<212> TYPE: DNA
<213> ORGANISM: human galanin receptor mRNA

<400> SEQUENCE: 6
cttggagtcg ctcccgttgc g                                               21

<210> SEQ ID NO 7
<211> LENGTH: 16
<212> TYPE: DNA
<213> ORGANISM: human galanin receptor mRNA

<400> SEQUENCE: 7
cttggagtcg ctcccg                                                     16

<210> SEQ ID NO 8
<211> LENGTH: 6
<212> TYPE: DNA
<213> ORGANISM: human galanin receptor mRNA

<400> SEQUENCE: 8 cttgga                                                                 6

<210> SEQ ID NO 9
<211> LENGTH: 15
<212> TYPE: DNA
<213> ORGANISM: human galanin receptor mRNA

<400> SEQUENCE: 9
ccctcgctga ggtcc                                                      15

<210> SEQ ID NO 10
<211> LENGTH: 18
<212> TYPE: DNA
<213> ORGANISM: rat-type 1 galanin receptor mRNA

<400> SEQUENCE: 10
caccgcagcc agttccat                                                   18

<210> SEQ ID NO 11
<211> LENGTH: 18
<212> TYPE: DNA
<213> ORGANISM: rat-type 1 galanin receptor mRNA

<400> SEQUENCE: 11
ggtcgctccc attccctt                                                   18

<210> SEQ ID NO 12
<211> LENGTH: 18
<212> TYPE: DNA
<213> ORGANISM: rat-type 1 galanin receptor mRNA

<400> SEQUENCE: 12
ggtcgctccc attccctt                                                   18

<210> SEQ ID NO 13
<211> LENGTH: 21
<212> TYPE: DNA
<213> ORGANISM: human galanin receptor cDNA

<400> SEQUENCE: 13
atggagctgg cggtcgggaa c                                               21
```

-continued

```
<210> SEQ ID NO 14
<211> LENGTH: 21
<212> TYPE: DNA
<213> ORGANISM: rat galanin receptor cDNA

<400> SEQUENCE: 14
ggcatggctg ctctccgtct g                                           21

<210> SEQ ID NO 15
<211> LENGTH: 21
<212> TYPE: DNA
<213> ORGANISM: rat galanin receptor cDNA

<400> SEQUENCE: 15
atggaactgg ctccggtgaa c                                           21

<210> SEQ ID NO 16
<211> LENGTH: 21
<212> TYPE: DNA
<213> ORGANISM: rat galanin receptor cDNA

<400> SEQUENCE: 16
ccattccctt cactgaggtt c                                           21
```

MEMBRANE-PERMEABLE CONSTRUCTS FOR TRANSPORT ACROSS A LIPID MEMBRANE

This application is a continuation of provisional application Ser. No. 60/053,678 filed Jul. 24, 1997.

FIELD OF THE INVENTION

The invention relates generally to the fields of molecular biology and cell biology. More specifically the invention relates to transport of membrane-permeable molecules across lipid membranes of cells into contact with targeted intracellular DNA and RNA sequences.

REFERENCES

Akhtar, S., Kole, R. and Juliano, R. "Stability of antisense DNA oligodeoxynucleotide analogs in cellular extracts and sera", Science 261:1004–12 (1991).

Akhtar, S. and Juliano, R. "Cellular uptake and intracellular fate of antisense oligonucleotides", Trends Cell. Biol. 2:139–44 (1992).

Alberts, B., Bray, D., Lewis, J., Raff, M., Roberts, K. and Watson, J. D. "The Plasma Membrane" in *Molecular Biology of the Cell*, 2nd Edition, Garland Publishing, Inc., New York, 1989, pp. 275–340.

Allinquant, B., Hantraye, P., Mailleux, P., Moya, K., Bouillot, C. and Prochiantz, A. "Down-regulation of amyloid precursor protein inhibits neurite outgrowth in vitro", *J. Cell Biol.* 128:919–27 (1994).

Andrus, A. in *Evaluating and Isolating Synthetic Oligonucleotides*, (1992), Applied Biosystems, Inc., Foster City, Calif.

Andrus, A., "Chemical methods for 5' non-isotopic labelling of PCR probes and primers" (1995) in *PCR 2: A Practical Approach*, McPherson, M., Hames, B., and Taylor, G. (eds.), Oxford University Press, Oxford, pp. 39–54.

Andrus, A. and Bloch, W., "HPLC of oligonucleotides and polynucleotides" (1998) in *HPLC of Macromolecules*, Oliver, R. W. A. (ed.), Oxford University Press, Oxford, pp. 141–70.

Azhayeva, E., Azhayev, A., Guzaev, A., Hovinen, J. and Lonnberg, H., "Looped oligonucleotides form stable hybrid complexes with a single-stranded DNA", Nucleic Acids Res., 23:1170–76 (1995).

Bartfai, T., "Galanin: a neuropeptide with important central nervous system actions" (1995) in *Psychopharmacology: the Fourth Generation of Progress*, Bloom, F. and Kupfer, D. (eds.), Raven Press, 1185 Ave of the Americas, New York, N.Y. 10036.

Beaucage, S. L. and Iyer, R. P. "Advances in the synthesis of oligonucleotides by the phosphoramidite approach", Tetrahedron 48:2223–2311 (1992).

Bennet, C. "Antisense Oligonucleotides: Is the Glass Half Full or Half Empty?", Biochem. Pharmacol. 55:9–19 (1998).

Bergot etal, "Spectrally resolvable rhodamine dyes for nucleic acid sequence determination", U.S. Pat. No. 5,366,860, issued Nov. 22, 1994.

Blackburn, G. M. and Gait, M. J. Eds. "DNA and RNA structure" in *Nucleic Acids in Chemistry and Biology, 2$^{nd}$ Edition*, (1996) Oxford University Press, pp. 15–81.

Bronstein, I. and Voyta, J., "Methods of using chemiluminescent 1,2-dioxetanes", U.S. Pat. No. 4,931,223, issued Jun. 5, 1990.

Bronstein, I., Fortin, J., Stanley, P., Stewart, G. and Kricka, L., "Chemiluminescent and bioluminescent reporter gene assays", Anal. Biochemistry, 219:169–81 (1994).

Cardullo etal, "Detection of nucleic acid hybridization by non-radiative fluorescence resonance energy transfer", Proc. Natl. Acad. Sci., 85:8790–8794 (1988).

Caruthers, M. and Beaucage, S., "Phosphoramidite compounds and processes" U.S. Pat. No. 4,415,732, issued Nov. 15, 1983.

Caruthers, M. and Matteucci, M., "Process for preparing polynucleotides", U.S. Pat. No. 4,458,066, issued July 3, 1984.

Chalfie, M. "Green fluorescent protein", Photochem. Photobiol., 62:651–56 (1995).

Clegg, R., "Fluorescence resonance energy transfer and nucleic acids", Meth. Enzymol., 211:353–388 (1992).

Dayhoff etal, in *Atlas of Protein Sequence and Structure, Suppl. 3*, Natl. Biomed. Res. Foundation, Washington, D.C., chapter 22, pp. 352–54.

Demers, D. "Method for enhancing amplification in the polymerase chain reaction employing peptide nucleic acid (PNA)", U.S. Pat. No. 5,629,178, issued May 13, 1997.

Demidov, V., Potaman, V., Frank-Kamenetskii, M., Egholm, M., Buchardt, O., Sonnichsen, S., and Nielsen, P. "Stability of peptide nucleic acids in human serum and cellular extracts", Biochem. Pharmacol., 48:1310–13 (1994).

Derossi, D., Joliot, A., Chassaing, G., and Prochiantz, A. "The third helix of the Antennapedia homeodomain translocates through biological membranes", J. Biol. Chem., 269:10444–50 (1994).

Derossi, D., Calvet, S., Trembleau, A., Brunissen, A., Chassaing, G., and Prochiantz, A. "Cell internalization of the third helix of the Antennapedia homeodomain is receptor-independent", J. Biol. Chem., 271:18188–93 (1996).

Dueholm, K., Egholm, M., Behrens, C., Christensen, L., Hansen, H., Vulpius, T., Petersen, K., Berg, R., Nielsen, P. and Buchardt, O., "Synthesis of peptide nucleic acid monomers containing the four natural nucleobases: Thymine, cytosine, adenine, and guanine and their oligomerization", J. Org. Chem., 59:5767–73 (1994).

Egholm, M., Buchardt, O., Nielsen, P. and Berg, R. "Peptide Nucleic Acids (PNA). Oligonucleotide analogues with an achiral peptide backbone", J. Amer. Chem. Soc., 114:1895–97 (1992).

Egholm, M, Buchardt, O. Christensen, L, Behrens, C, Freier, S., Driver, D., Berg, R., Kim, S. "PNA hybridizes to complementary oligonucleotides obeying the Watson-Crick hydrogen bonding rules", Nature, 365:566–68 (1993).

Geiser, T., Beilan, H., Bergot, J. and Otteson, K. "Automation of solid-phase peptide synthesis" in *Macromolecular Sequencing and Synthesis*, Alan R. Liss, Inc., 1988, pp. 199–218.

Goodchild, J., "Enhancement of ribozyme catalytic activity by a contiguous oligodeoxynucleotide (facilitator) and by 2'-O-methylation", Nucleic Acids Research, 20:4607–12 (1992).

Habert-Ortoli, E., Amiranoff, B., Loquet, I., Laburthe, M. and Mayaux, J. "Molecular cloning of a functinal human galanin receptor", Proc. Natl. Acad. Sci USA, 91:9780–83 (1994).

Hanka, L, Dietz, A., Gerpheide, S., Kuentzel, S. and Martin, D. "CC-1065, a new antitumor antibiotic. Production, in vitro biological activity, microbiological assays and taxonomy of the producing microorganism", J. Antibiotics, 31:1211 (1978).

Hanvey, J. et al. "Antisense and antigene properties of peptide nucleic acids" Science 258:1481–1485 (1992).

Helene, C. and Toulme, J. "Specific regulation of gene expression by antisense, sense and antigen nucleic acids" Biochim. Biophys. Acta, 1049:99–125 (1990).

Hermanson, G. T., in *Bioconjugate Techniques*, (1996) Academic Press, San Diego, pp. 4055, 643–671.

Houseal, T., "Diagnosis of genetic disorders" in *DNA Probes,* 2$^{nd}$ Edition, Stockton Press, New York, 1993, pp. 411–81.

Knudsen, H. and Nielsen, P. "Antisense properties of duplex- and triplex-forming PNAs", Nucl. Acids Res., 24:494–500 (1996).

Knudsen, H. and Nielsen, P. "Application of peptide nucleic acid in cancer therapy", Anticancer Drug, 8:113–18 (1997).

Kumar, S. etal, "Solution structure of a highly stable DNA duplex conjugated to a minor groove binder", Nucleic Acids Res. 26:831–38 (1998).

Lamond, A., Sproat, B., Ryder, U., Hamm, J., "Probing the structure and function of U2 snRNP with antisense oligonucleotides made of 2'-O-Me RNA" Cell, 58:383–90 (1989)

Langel, Ü., Land, T. and Bartfai, T. "Design of chimeric peptide ligands to galanin receptors and substance P receptors", Int. J. Pept. Protein Res., 39:516–22 (1992).

Langel, Ü., Pooga, M., Kairane, Z., Zilmer, M. and Bartfai, T. "A galanin-mastoparan chimeric peptide activates the Na$^+$, K$^+$ ATPase and reverses its inhibition by ouabain", Regul. Pept. 62:47–52 (1996).

Livak, K., Flood, S., Marmaro, J., Giusti, W., and Deetz, K., "Oligonucleotides with fluorescent dyes at opposite ends provide a quenched probe system useful for detecting PCR product and nucleic acid hybridization". PCR Methods and Applications, 4:357–362 (1995).

Loakes, D and Brown, D. "5-Nitroindole as a universal base analogue", Nucleic Acids Research, 22:4039–43 (1994).

Menchen etal, "4,7-Dichlorofluorescein dyes as molecular probes", U.S. Pat. No. 5,188,934, issued Feb. 23, 1993.

Meyer, R., Gall, A., and Reed, M., "Peptide linkers for improved oligonucleotide delivery", WO 94/13325, international publication date: Jun. 23, 1994.

Morvan F., Rayner, B., Imbach, J., Chang, D., Lown, J., "α-DNA I. Synthesis, Characterization by high field $^1$H-NMR, and base-pairing properties of the unnatural hexadeoxyribonucleotide α-[d(CpCpTpTpTpCpC)] with its complement β-[d(GpGpApApGpG)], Nucleic Acids Research, 14:5019–35 (1986).

Nichols, R., Andrews, P., Zhang, P., Bergstrom, D., "A universal nucleoside for use at ambiguous sites in DNA primers", Nature, 369:492–3 (1994).

Nielsen, P. E., Egholm, M., Berg, R. H., and Buchardt, O., "Sequence-selective recognition of DNA by strand displacement with a thymidine-substituted polyamide", Science 254:1497–1500 (1991).

Nielsen, P. E., Egholm, M., Berg, R. H. & Buchardt, O. "Peptide nucleic acids (PNAs): Potential Antisense and Anti-gene Agents", Anti-Cancer Drug Design 8:53–63 (1993).

Ohtsuka, E. etal, "Compounds for the cleavage at a specific position of RNA, oligomers employed for the formation of said compounds, and starting materials for the synthesis of said oligomers", U.S. Pat. No. 5,013,830, issued May 7, 1991.

Ørum, H., Nielsen, P., Egholm, M., Berg, R., Buchardt, O., and Stanley, C. "Single base pair mutation analysis by PNA directed PCR clamping", Nuc. Acids Res. 21:5332–36 (1993).

Peffer, N., Hanvey, J., Bisi, J., Thomson, S., Hassman, C., Noble, S. and Babiss, L. "Strand-invasion of duplex DNA by peptide nucleic acid oligomers", Proc. Natl. Acad. Sci. USA 90:10648–52 (1993).

Perbost etal, *Biochem. Biophys. Res. Comm.,* 165:742- (1989)

Perseptive Biosystems, "Identifying point mutations by PNA-directed PCR clamping" (1995).

Peterson, G. L. "A simplification of the protein assay method of Lowry et al which is more generally applicable", Anal. Biochem. 83:346–56 (1977).

Pooga, M., Hällbrink, M., Zorko, M. and Langel, Ü. "Cell penetration by transportan", FASEB J. 12:67–77 (1998).

Pooga, M., Juréus, A., Rezaei, K., Hasanvan, H., Saar, K., Kask, K., Kjellen, P., Land, T., Halonen, J., Maeorg, U., Uri, A., Solyom, S., Bartfai, T., Langel, Ü. "Novel galanin receptor ligands" J. Pept. Res. 51(1), 65–74 (1998).

Roush, W. "Antisense aims for a renaissance", Science 276:1192–93 (1997).

Sproat, B. "Synthesis of 2'-O-alkyl oligoribonucleotides", in *Protocols for Oligonucleotides and Analogs* (1994) Agrawal, S., Ed., Humana Press.

Stein, C. and Cohen, J. "Oligodeoxynucleotides as inhibitors of gene expression: a review", Cancer Res. 48:2659–68 (1988).

Stein, C, and Cheng, Y. "Antisense oligonucleotides as therapeutic agents: is the bullet really magical?", Science (Washington, D.C.), 261:1004–12 (1993).

Stryer, L. "Generation and storage of metabolic energy" in *Biochemistry,* 2nd Edition, W.H. Freeman and Company, San Francisco, 1981, pp. 343–345.

Theisen, P., McCollum, C., and Andrus, A. "Fluorescent dye phosphoramidite labelling of oligonucleotides", *Nucleic Acid Symposium Series No. 27*, Oxford University Press, Oxford, pp. 99–100 (1992).

Troy, C., Derossi, D., Prochiantz, A., Greene, L. and Shelanski, M. "Down-regulation of Cu/Zn superoxide dismutase leads to cell death via the nitric oxide-peroxynitrite pathway", J. Neurosci. 16:253–61 (1996).

Uhlmann, E., Will, D., Breipohl, G., Langner, D. and Ryte, A., "Synthesis and properties of PNA/DNA chimeras", Angew. Chem. Int. Ed. Engl. 35:2632–35 (1996).

Van der Laan, A. etal, "A convenient automated solid-phase synthesis of PNA-(5')-DNA-(3')PNA chimera", Tetrahedron Lett., 38:2249–52 (1997).

Vinayak, R. etal, "Automated chemical synthesis of PNA-DNA chimera on a nucleic synthesizer", Nucleosides & Nucleotides, 16:1653–56 (1997).

Walker, I., Irwin, W., and Akhtar, S., "Improved cellular delivery of antisense oligonucleotides using transferrin receptor antibody-oligonucleotide conjugates", Pharmaceutical Res., 12:1548–53 (1995).

Wiederholt, K., Rajur, S., Giuliano, J., O'Donnell, M. and McLaughlin, L., "DNA-Tethered Hoechst groove-binding agents: Duplex stabilization and fluorescence characteristics", J. Am. Chem. Soc., 118:7055–62 (1996).

Yakubov, L., Deeva, E., Zarytova, V., Ivanova, E., Ryte, A., Yurchenko, L. and Vlassov, V. "Mechanism of oligonucleotide uptake by cells: involvement of receptors?" Proc. Natl. Acad. Sci. USA, 86:6454 (1989).

Zorko, M., Pooga, M., Saar, K., Rezaei, K., Langel, Ü. "Differential regulation of GTPase activity by mastoparan and galparan", Arch. Biochem. Biophys., 349:321–328 (1998).

Zuckermann, R., Kerr, J., Kent, S., Moos, W., "Efficient method for the preparation of peptoids [oligo(N-substituted glycines)] by submonomer solid-phase synthesis", J. Amer. Chem. Soc., 114:10646–47 (1992).

BACKGROUND

Delivery of oligonucleotides, nucleic acids and nucleic acid analogs inside cells is a fundamental requirement for their therapeutic efficacy as antisense agents (Yakubov, 1989). The main problems with available antisense reagents are their low intracellular stability and inefficient cellular uptake (Stein, 1993). Furthermore, the high doses of antisense reagents required for therapeutic action lead often to toxic side effects. These drawbacks can be circumvented by applying modified nuclease resistant oligonucleotides (Bennet, 1998) or enhancing intracellular delivery of antisense oligonucleotides. Because of its hydrophobic interior, the lipid bilayer of the plasma membrane is a highly impermeable barrier to most polar and charged molecules (Alberts, 1989). Many antisense nucleic acids falter as potential drug candidates by not attaining effective pharmacokinetics, i.e. effective intracellular concentrations.

The antisense approach relies on delivery of specific nucleic acid or nucleic acid analog sequences to inhibit the expression or replication of DNA at the transcriptional level ("antigene"), or mRNA at the translational level ("antisense"). From the many studies on the antigene and antisense mechanisms of action, it is clear that cellular uptake and distribution are key to therapeutic action (Helene, 1990; Akhtar, 1992; Stein, 1993). The present invention achieves improvements in these important parameters.

In view of the limitations and deficiencies of conventional constructs of peptides and nucleic acid analogs, and inadequate methods for intracellular delivery across membranes, it is of interest to develop novel constructs with membrane-permeable properties. Constructs containing peptide and peptide analog sequences that are transported across lipid membranes rapidly and in high concentration are desirable. Nucleic acid analogs moieties of constructs which can be released after transport and interact with target molecules are very desirable. Furthermore, it is desirable to provide cleavable linkers between the peptide and nucleic acid analogs moieties of the constructs.

Nucleic acid analogs which can hybridize to target polynucleotides are especially desirable. Hydrophobic, uncharged nucleic acid analogs are preferable as nucleic acid analogs moieties. Efficient methods for synthesis and purification of constructs are desirable. The invention herein provides for solutions for some of the limitations and deficiencies in transport and targetting of molecules into cells via optimized constructs and methods.

SUMMARY

The present invention is directed towards novel constructs of peptides and nucleic acid analogs conjugated together for transport across a lipid membrane and for delivery into interactive contact with intracellular polynucleotides such as RNA, DNA, enzymes, receptors, and regulatory elements. Transport is effected through the membrane of a cell, and through the walls of certain subcellular structures, including the nucleus, mitochondria, ribosomes, etc.

The present invention includes two peptides which increase the intracellular distribution of nucleic acid analogs, e.g. PNA: (i) transportan, galanin (1–12)-Lys-mastoparan (1–14) amide (Pooga, 1998), and (ii) pAntennapedia, pAntp(43–58) (Allinquant, 1994; Troy, 1996; Derossi, 1996). Both peptides have been shown to enter cells in an energy and receptor independent manner. Many other proteins may be conjugated with nucleic acid analogs and employed for their membrane-permeable properties (Alberts, 1989), e.g. Green fluorescent protein (Chalfie, 1995) and conservative variants thereof.

Generally, the peptide moiety in the construct of the present invention comprises the sequence of amino acids:

INLKALAALAKKIL                (SEQ. ID NO. 1)

following the one-letter amino acid code (Table 1) and wherein the C-terminal preferably is functionalized to form an amide group, homologs thereof, conservative variants thereof, or peptide analogs thereof which retain the membrane permeant property of the sequence. Preferably, the peptide further comprises the amino acid sequence:

GWT and more preferably the sequence further comprises the amino acid sequence:

GWTLNSAGYLLG              (SEQ. ID NO. 2)

The currently most preferred peptide for imparting this cell membrane permeant property has the amino acid sequence is the peptide referred to as transportan or galparan (Pooga, 1998):

GWTLNSAGYLLGKINLKALAAL
  AKKIL-amide.               (SEQ. ID NO. 3)

Preferably, the nucleic acid analog molecule which is conjugated to this peptide is joined to the first (from N to C, or left to right) lysine residue, K, through a labile bond, such as a disulfide bond joining a pair of cysteine residues. For stability, and ease of synthesis and purification, the C-terminus carboxyl group is typically converted to the amide, via the appropriate synthesis support linker.

A first aspect of the present invention is a construct comprising a nucleic acid analog moiety which hybridizes with complementary target sequences in the cell. The nucleic acid analog may be any type proposed for use or used in antisense technology, e.g. a peptide nucleic acid (PNA).

In a preferred embodiment, the nucleic acid analog undergoes hybridization with complementary, intracellular polynucleotides. The invention provides constructs comprising hybridizing nucleic acid analogs moieties such as PNA, PNA-DNA chimera, or a PNA-nucleic acid analog chimera which can hybridize with a complementary sequence of an intracellular polynucleotide. The most preferred nucleic acid analog is a peptide nucleic acid (PNA) of the type with a 2-aminoethylglycine backbone (Nielsen etal, 1991).

In a second aspect of the invention, the nucleic acid analog may be comprised of modifications to the internucleotide linkage, the sugar, or nucleobase moieties of a nucleic acid. Examples of suitably modified nucleic acid analogs are 2'-O-methyl and other 2'-O-alkyl oligoribonucleotides; phosphorothioate and other phosphate analogs; and the like. The nucleic acid analog is selected for several properties, including (i) high specificity, (ii) high affinity, (iii) non-extendability by polymerase, (iv) chemical stability, and (v) nuclease-resistance. In a preferred embodiment, the nucleic acid analogs is a PNA (peptide-nucleic acid) oligomer (Nielsen, 1991). To improve solubility and reduce aggregation effects, the PNA nucleic acid analogs may be conjugated with hydrophilic modifiers, such as polyethyleneoxy, peptides, nucleic acids, nucleic acid analogs, and the like.

In a third aspect, the nucleic acid analog of the present invention is coupled to a peptide which effects transport across a lipid membrane and then permits presentation of the nucleic acid analog to intracellular polynucleotides, whereby duplex or triplex structures are formed. In a preferred embodiment of this aspect of the present invention, the hybridizing nucleic acid analog and the transport-effecting peptide are attached by a bond which is labile in the intracellular environment so that the hybridizing nucleic acid analog is cleaved and released, thereby physically separating the nucleic acid analog and peptide moieties. An example of a labile bond is a disulfide bond whereupon exposure to an endogenous intracellular enzyme or reducing agent, such as glutathione or NADPH, the disulfide bond is broken or cleaved, separating the peptide and nucleic acid analogs moieties (Stryer, 1981). Constructs with a disulfide group between cysteine amino acid residues bound to the nucleic acid analogs and the peptide are preferred embodiments and conveniently prepared, and appropriately labile, to release the nucleic acid analogs for hybridization with target polynucleotides. Other labile bonds to link the nucleic acid analogs and peptide moieties include ester (—$CO_2$—), carbamate (—$NHCO_2$—), and sulfonate (—$SO_3$—), which may release the nucleic acid analogs by enzymatic catalysis or by hydrolysis (Meyer, 1994).

In a fourth aspect of the invention, methods and particular sets of constructs are provided which may be used to selectively block DNA transcription, RNA translation, RNA or DNA expression, DNA replication, RNA reverse-transcription, or DNA or RNA regulatory function of intracellular polynucleotides, e.g., for research purposes as an aid in discerning a structure/functional relationship at the molecular level or for therapeutic purposes. Generally, the method comprises the steps of providing one or a set of nucleic acid analogs, which hybridize with the one or a subset of intracellular polynucleotide sequences. These constructs are exposed to a cell, and can be effective at concentrations as low as 10 nM or lower, as they transport across cell membranes, become exposed directly for hybridization or other interactive contact to intracellular molecules in the cytosol and various subcellular compartments, and hybridize with target DNA or RNA, typically at least temporarily inhibiting or blocking the normal function of the intracellular polynucleotide.

In a fifth aspect, the present invention includes a chimera conjugated with a stabilizing moiety which serves to increase intermolecular duplex stability, provide enhanced detectablity, and/or capturability. Preferred moieties for increasing intermolecular duplex stability include minor groove binders, such as Hoechst 33258 (Wiederholt, 1996), CC-1065 (Hanka, 1978), CDPI3 (Kumar, 1998), and intercalators, such as acridine, ethidium bromide, spermine, polycations and the like (Blackburn, 1996).

To increase the detectability of the construct or nucleic acid analogs, the nucleic acid analogs can be conjugated to a label, e.g. a fluorescent dye including fluorescein, rhodamine, cyanine, and the like. To facilitate detection, capture or immobilization, a construct may be conjugated with biotin, digoxigenin, or peptides. The label may be attached to the chimera using any number of known conjugation methods (Andrus, 1995; Hermanson, 1996).

A sixth aspect of the invention provides a method for accurate, real time monitoring, by in situ detection, of fluorescent-labelled constructs interacting with targetted intracellular molecules by specifying fluorescent reagents for generating a stable fluorescent signal proportional to the amount of transcriptional or translational inhibition (Houseal, 1993). The intracellular location of the delivered constructs can be localized and imaged within certain organelles and features, such as the nucleus, mitochondria, membranes, and the like. Similarly, chemiluminescent-labelled constructs can be triggered to emit light and provide similar detection signals. Adamantyl 1,2-dioxetane-labelled constructs may be ring-opened upon dephosphorylation by alkaline phosphatase, generating light measurable by a luminometer, or other light-gathering or light-sensitive device (Bronstein, 1990; Bronstein, 1994).

Hybridization of fluorescer and quencher labelled constructs may give a fluorescence resonance energy transfer (FRET) effect, yielding quantitative information about copy number and expression levels of certain genes and sequences (Clegg, 1992; Cardullo, 1988; Livak, 1995).

Those skilled in the art will appreciate that while the invention presented here is embodied as specific sequences of amino acids discovered to be effective to induce membrane transport, that certain homologs, truncated proteins, fusion proteins, conservative variants, species variants, and other related constructs characterized by different amino acid sequences but which retain the membrane permeant activity of the sequences disclosed herein can be made without the exercise of invention, and properly should be considered included as one of the embodiments of the invention here disclosed.

DEFINITIONS

Unless stated otherwise, the following terms and phrases as used herein are intended to have the following meanings:

A "nucleotide" is a monomer unit in a polymeric nucleic acid, such as DNA or RNA, and is composed of three distinct subparts or moieties: sugar, phosphate, and nucleobase (Blackburn, M., 1996). When part of a duplex, nucleotides are also referred to as "bases" or "base pairs". The most common naturally-occurring nucleobases, adenine (A), guanine (G), uracil (U), cytosine (C), and thymine (T) bear the hydrogen-bonding functionality that binds one nucleic acid strand to another in a sequence specific manner. "Nucleoside" refers to a nucleotide that lacks a phosphate. In DNA and RNA, the nucleoside monomers are linked by phosphodiester linages, where as used herein, the term "phosphodiester linkage" refers to phosphodiester bonds or bonds including phosphate analogs thereof, including associated counterions, e.g., $H^+$, $NH_4^+$, $Na^+$, and the like.

"Polynucleotide" or "oligonucleotide" refer to linear polymers of natural nucleotide monomers or analogs thereof, including double and single stranded deoxyribonucleotides "DNA", ribonucleotides "RNA", and the like. In other words, an "oligonucleotide" is a chain of deoxyribonucleotides or ribonucleotides, that are the structural units that comprise deoxyribonucleic acid (DNA) and ribonucleic acid (RNA), respectively. Polynucleotides typically range in size from a few monomeric units, e.g. 8–40, to several thousand monomeric units. Whenever a DNA polynucleotide is represented by a sequence of letters, such as "ATGCCTG," it will be understood that the nucleotides are in 5'→3' order from left to tight and that "A" denotes deoxyadenosine, "C" denotes deoxycytidine, "G" denotes deoxyguanosine, and "T" denotes thymidine, unless otherwise noted.

"Nucleic acid analogs" are structurally modified, polymeric analogs of DNA and RNA made by chemical synthesis from monomeric nucleotide analog units, and possessing some of the qualities and properties associated with nucleic acids. PNA and phosphorothioate oligonucleotides are examples of two of many nucleic acid analogs known in the art. "Watson/Crick base-pairing" and "Watson/Crick complementarity" refer to the pattern of specific pairs of nucleotides, and analogs thereof, that bind together through hydrogenbonds, e.g. A pairs with T and U, and G pairs with C. The act of specific base-pairing is "hybridization" or "hybridizing". A hybrid forms when two, or more, complementary strands of nucleic acids or nucleic acid analogs undergo base-pairing.

"Conjugate" or "conjugated" refer to a covalent, ionic, or hydrophobic interaction whereby the moieties of a molecule are held together and preserved in proximity.

"Linker" refers to one or more atoms comprising a chain connecting a nucleic acid analog to a moiety such as a peptide, label, modifier, stabilizing group, or the like.

"Chimera" as used herein refers to an oligonucleotide including one or more nucleotide and one or more nucleotide analog units. The monomer units are linked through phosphodiester and phosphodiester analog linkages.

"Phosphodiester analog" or "internucleotide analog" refer to analogs of natural phosphodiester 3',5'-internucleotide linkages differing in their composition and/or location of attachment to a nucleotide, including but not limited to 2',5'-linkage, 3',3'-linkage, 5',5' linkage, methyl phosphonate, alkylated phosphotriester, 3'-N-phosphoramidate, and non-bridging N-substituted phosphoramidate.

The term "2'-modified RNA" means a nucleic acid analog containing one or more ribonucleotides in a which a 2' position on a sugar bears a substituent replacing a hydroxyl. As an example, 2'-O-alkyl RNA comprises a nucleic acid analog containing one or more ribonucleotides in which a 2' position on a sugar consists of the moiety —OR where R is lower alkyl (Sproat, 1994).

The terms "permeant" and "permeable" refer to the ability of a construct of the present invention to pass through a cellular membrane, or ascribed as characteristics of the susceptibility of cellular membranes to have constructs pass through them (Alberts, 1989).

"Label" refers to a group covalently attached at one or both termini of the nucleobase oligomer. The label is capable of conducting a function such as giving a signal for detection of the molecule by such means as fluorescence, chemiluminescence, and electrochemical luminescence. Alternatively, the label allows for separation or immobilization of the molecule by a specific or non-specific capture method (Andrus, 1995). Labels include, but are not limited to, fluorescent dyes, such as fluorescein and rhodamine derivatives (Menchen, 1993; Bergot, 1994), cyanine dyes, and energy-transfer dyes (Clegg, 1992; Cardullo, 1988).

"Detection" refers to detecting, observing, or measuring a construct on the basis of the properties of a detection label.

The term "labile" refers to a bond or bonds in a molecule with the potentiality of being cleaved by reagents, enzymes, or constituents of a cell.

The term "nucleobase-modified" refers to base-pairing derivatives of A,G,C,T,U, the naturally occurring nucleobases found in DNA and RNA.

"Peptides" are polymers of amino acids of which the written convention is N, or amino, terminus is on the left and the C, or carboxyl, terminus is on the right. The 20 most common, natural L-amino acids are alternatively designated by three-letter or one-letter codes (Table 1). Peptides, as used herein, are considered to include "peptide analogs", structural modifications containing one or more modifications to L-amino acid side-chains or to the α-amino acid backbone. An example of a backbone modified peptide analog is the N-methyl glycine "peptoid" (Zuckermann, 1992).

TABLE 1

Three-letter and one-letter amino acid code

| Amino Acid | Three letter | One letter |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acid residues that are "conservative variants" or "conservative substitutions" for corresponding residues in a reference sequence are those that are physically or functionally similar to the corresponding reference residues, e.g. that have similar size, shape, electric charge, hydrophobicity, hydrophilicity, polarity, reactive chemical properties including the ability to form covalent or hydrogen bonds, and other properties. Particularly preferred conservative variants are those fulfilling the criteria defined for an "accepted point mutation" (Dayhoff, 1978). Conservative variants of amino acids typically include substitutions within the following groups:

I. glycine, alanine, valine, isoleucine, leucine

II. aspartic acid, glutamic acid, asparagine, glutamine

III. serine, threonine

IV. lysine arginine

V. phenylalanine, tyrosine

"Homologs" are peptides with substantially identical amino acid sequences which retain the lipid membrane-permeant function and which differ from the preferred sequences mainly or only by conservative amino acid substitutions, for example, substitution of one amino acid for another within the same class above, e.g. I. valine for glycine or IV. arginine for lysine) or by one or more non-conservative substitutions, deletions, or insertions located at positions of the amino acid sequence which do not destroy the function of the protein. Preferably, such a sequence is at least 85%, and more preferably 90%, and most preferably 95% identical at the amino acid level to the sequence of the peptide to which it is being compared.

BRIEF DESCRIPTION OF THE DRAWINGS

FIG. 1 shows segments of DNA and PNA structures.

FIG. 4 shows structures of two constructs: pAntp(43–58)-S-S-(biotinyl PNA21) A and transportan-S-S-(biotinyl PNA21) B.

FIG. 6 shows data of down-regulation of $^{125}$K-galanin binding to human galanin receptors in Bowes cellular membranes by the cPNA oligomers, cPNA-peptide constructs, phosphorothioates, oligonucleotides complementary to human and/or GalR1 mRNA and the transport peptides. The half maximal inhibitory effects in $\mu$M are listed. CPNAr and cPNAh denote the complementary PNA sequences of the coding regions of rat and human GalR1 mRNA, respectively. Sequences of PNA oligomers are presented in the accordance with the peptide nomenclature of N-terminus on the left and the C-terminus on the right. The C-terminus is amidated is all examples.

FIG. 7 shows the concentration dependence of down-regulation of GalR1 by the constructs of antisense PNA with carrier peptides transportan and pAntp. Bowes cells are grown in the presence of the constructs for 36 h at 37° C. and the amount of receptors is estimated as specific binding of $^{125}$I-galanin to the cellular membranes and by Western blot. Cells treated with:

○ cPNAh(18–38)-S-S-pAntp A
  ● cPNA h(18–38)-S-S-transportan B
  ■ cPNA h(1–21)-S-S-pAntp
  ▲ phosphorothioate h(18–38)
  Δ scrambled PNA h(18–38)-S-S-pAntp
  ▽ cPNA h(18–38)

Figure 8:
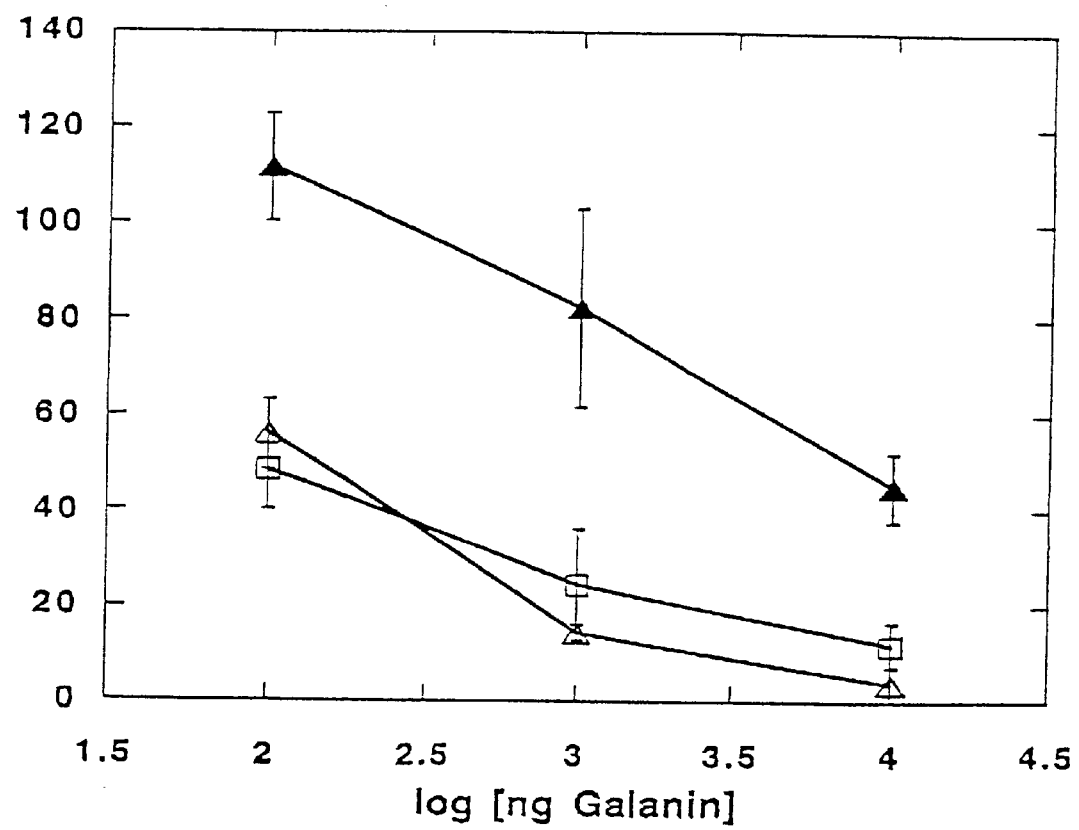

FIG. 8 shows the effects of various doses of intrathecal galanin on the reflex facilitatory effect of C-fiber Conditioning Stimulation (CS) in 7 untreated rats (□), 3 rats receiving the construct of scrambled PNA r(18–38)-S-S-pAntp (Δ), and 5 rats receiving the construct of cPNA r(18-38)-S-S-pAntp (▲). The data is presented as % of control facilitation following the CS without preceding galanin treatment.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. STRUCTURE AND SYNTHESIS OF NUCLEIC ACID ANALOGS

Generally, the design and synthesis of the nucleic acid analogs of the invention follows conventional teachings. Preferably, nucleic acid analogs are synthesized on an automated, solid-phase DNA synthesizer using phosphoramidite chemistry (Beaucage etal, 1992; Caruthers, 1983), e.g. ABI 392 or 394 DNA synthesizer (PE Applied Biosystems, Foster City, Calif.) or on an automated, solid-phase peptide synthesizer, e.g. ABI 433 Peptide synthesizer (PE Applied Biosystems, Foster City, Calif.).

PNA

A preferred nucleic acid analog of the present invention is peptide nucleic acid (PNA), a particularly promising class of nucleic acid analogs with potential utility as the next generation antisense reagents (Nielsen, 1991; Bennet, 1998). The PNA utilize the natural nucleobases that undergo Watson/Crick base-pairing, linked through a neutral, achiral, poly[2-aminoethylglycine] amide backbone resulting in superior hybridization properties, i.e. extremely high specificity and affinity (Egholm, 1993; Peffer, 1993). The PNA are not substrates for any known nucleases, proteases, peptidases, or other modifying enzymes (Demidov etal, 1994), an important property since native nucleic acids, DNA and RNA, are rapidly degraded by nucleases and thereby fail to effect favorable in vivo antigene or antisense results (Akhtar, 1991). Through hybridization to the target polynucleotide, the so formed hybrid duplexes, PNA/DNA and PNA/RNA, may effectively inhibit normal functioning of the intracellular DNA at the transcriptional level and RNA at the translational level. PNA have been applied to block protein expression on the transcriptional and translational levels, and microinjected PNA demonstrates a strong antisense effect in intact cells (Knudsen, 1996; Knudsen, 1997). PNA oligomers have also found utility in genetic analysis and diagnostic tests as enhanced probes, and in molecular biology tools, such as enhancing the fidelity of polymerase activity in PCR (Demers, 1997). Furthermore, PNA has been used in PCR as a "clamping element" for single base-pair mutation analysis (Ørum, 1993) whereby PNA suppresses amplification of complementary target sequences, typically wild-type, allowing the selective amplification of low-copy number or mutant target sequences with competing DNA primers. PNA oligomers by themselves are not efficiently delivered or transported into the cellular interior which has until now hindered the in vivo application of PNA as antisense reagents (Nielsen, 1993; Hanvey, 1992; Knudsen, 1997).

Figure 2:
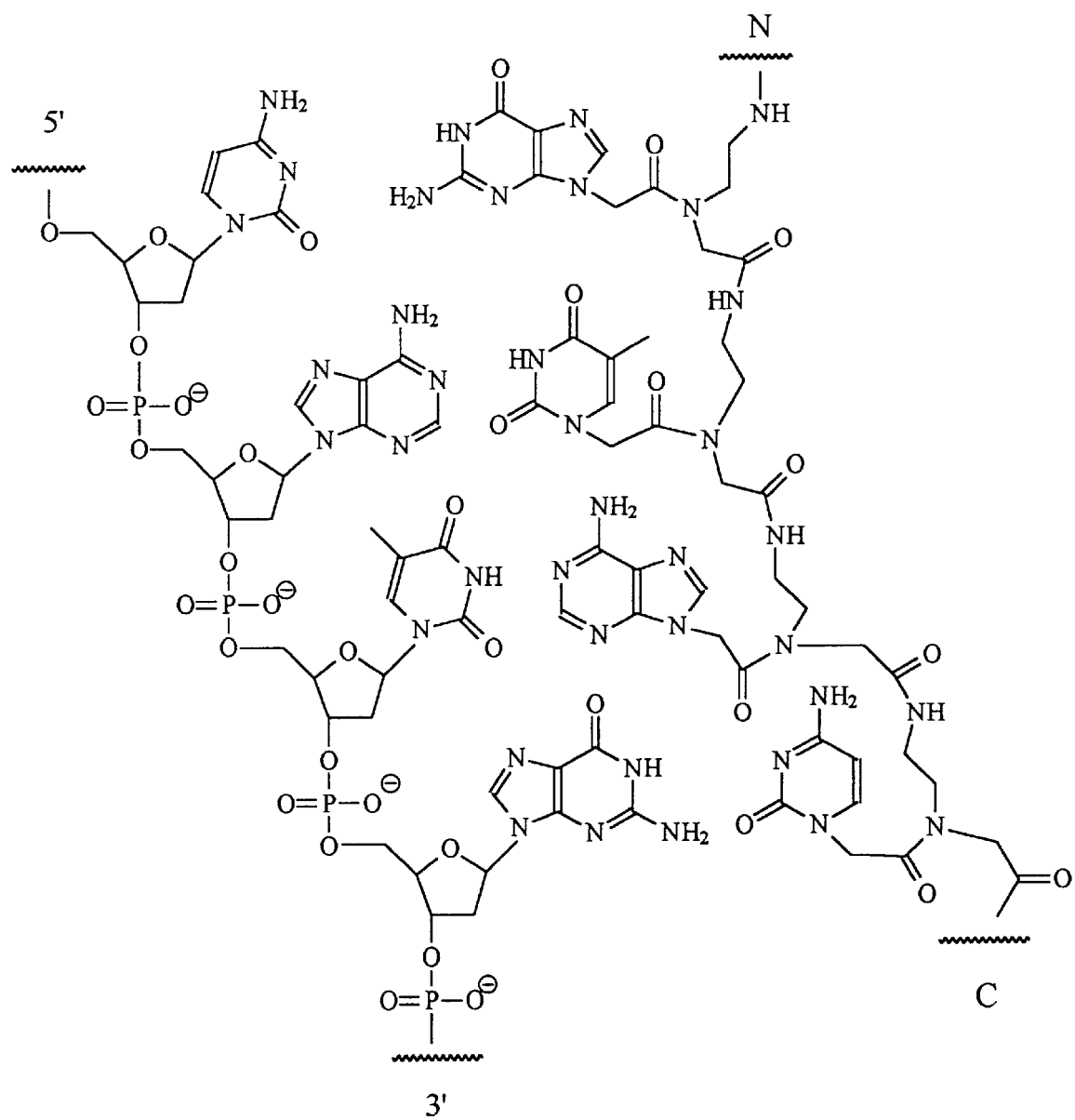
FIG. 2 shows base-pairing in a segment of a DNA/PNA duplex. PNA is oriented in the more stable antiparallel configuration where the N-terminus of PNA is aligned with the 5' terminus of DNA, and the C-terminus of PNA is aligned with the 3' terminus of DNA.

FIG. 1 is a comparison of the structures of DNA and PNA. As illustrated, the sugar-phosphate backbone of natural DNA is replaced by the 2-aminoethylglycine peptide backbone in PNA with retention of the DNA nucleobases. A hybrid duplex between PNA and DNA shown in FIG. 2 illustrates the Watson-Crick base pairing in a DNA/PNA duplex (Egholm, 1993). The remarkably high affinity of PNA for DNA targets, as exemplified by high thermal melting values ($T_m$) of duplexes of PNA and nucleic acids, is due largely to the non-ionic character of PNA which obviates the electronic repulsion between strands in DNA/DNA and DNA/RNA duplexes. PNA oligomers are stable both hydrolytically and to enzymatic degradation within cells. PNA oligomers are not substrates for any known nucleases, polymerases, peptidases, or other enzymes which may render other nucleic acids or nucleic acid analogs inactive by degradation or processing. PNA oligomers can be synthesized by conventional methods on commercially available, automated synthesizers, e.g. the Model 394 DNA/RNA synthesizer or Model 433 Peptide synthesizer (PE Applied Biosystems, Foster City, Calif.), with commercially available reagents (Vinayak, 1997; Van der Laan, 1997).

Modified Sugar Analogs

In a first embodiment, the sugar moiety of a fraction of the nucleotides of a nucleic acid analog is modified. In a particularly preferred embodiment, the 2'-position of a nucleoside is modified. Oligonucleotides bearing 2'-modified nucleosides have been studied as ribozymes, nuclease-resistance antisense analogs, and other cellular mechanism probes (Lamond, 1989; Goodchild, 1992). Desirable features of 2'-O-alkyl-oligoribonucleosides include high chemical stability, substantial RNA- and DNA-nuclease resistance (including RNaseH), and increased thermal duplex stability (Ohtsuka, 1991).

In a preferred embodiment, a fraction of the ribonucleotides are 2'-O-alkylribonucleotides, preferably 2'-O-methyl-ribonucleotides. Additional preferred modified ribonucleotides include 2'-O-allyl-ribonucleotides, 2'-allyl ribonucleotides, 2'-halo-ribonucleotides, 2'-O-methoxyethyl-ribonucleotides, 2'-branching group-ribonucleotides, and 2'-O-branching group-ribonucleotides. The structure below illustrates several preferred sugar modifications.

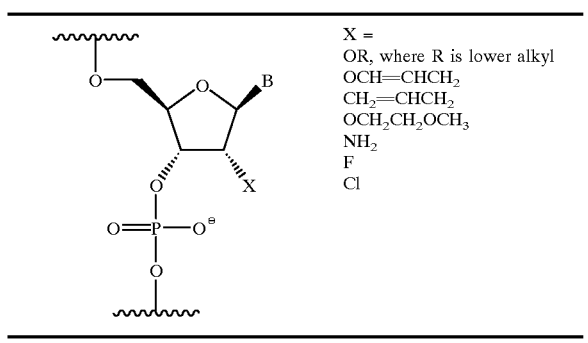

X =
OR, where R is lower alkyl
OCH=CHCH$_2$
CH$_2$=CHCH$_2$
OCH$_2$CH$_2$OCH$_3$
NH$_2$
F
Cl In another embodiment of the invention, one or more nucleotides are modified at the 1'-position. In a preferred modification, the 1'-position includes an α-anomeric nucleotide base, in which the natural sterochemistry of the 1'-position of the sugar is inverted, i.e., the heterocycle and 5'-atom are in a trans orientation instead of a cis orientation (Morvan, 1986). The 1'-position may also bear a branching group (Azhayeva, 1995). Alternatively, the modified sugar analog is a carbocyclic-nucleotide in which the 4'-oxygen atom of the sugar is replaced with a carbon, sulfur, or nitrogen atom (Perbost, 1989).

Modified Internucleotide analogs

In another preferred embodiment, some or all of the nucleotides making up the nucleic acid analog moiety are linked through nonstandard internucleotide linkages. Preferred nonstandard internucleotide linkages include 2'-5'-linkages, inverted 3'-3' and 5'-5' linkages, methyl phosphonate, non-bridging N-substituted phosphoramidate, alkylated phosphotriester branched structures, 3'-N-phosphoramidate, peptide nucleic acid (PNA), and non-nucleosidic polymer. The term "non-nucleosidic polymer" refers to a polymer which is not a polynucleotide, e.g., polyethylene oxide, polypeptide, polyacrylamide, and polycarbohydrate.

More preferably, the linkages are PNA or 3'-N-phosphoramidate due to the high affinity of nucleic acid analogs including such linkages.

Nucleobase Analogs

In yet another preferred embodiment of the present invention, some or all of the nucleotides in the nucleic acid analogs include modified nucleobases. Preferred nucleobase modifications include C-5-alkyl pyrimidine, 2,6-diaminopurine, 2-thiopyrimidine, C-5-propyne pyrimidine, 7-deazapurine, isocytosine and isoguanine, and universal base, which shows diminished base-specific discrimination in a Watson/Crick, base-pairing hybridization interaction, e.g., 3-nitropyrrole (Nichols, 1994) and 5-nitroindole (Loakes, 1994).

5'- and 3'-End Modification

In a third aspect of the present invention, improved physiochemical and biological properties of chimeric vectors are achieved by modifying the 5'- and 3'-ends of the chimera. Specifically, such modifications provide for increased resistance to nuclease degradation. In a preferred embodiment of this aspect, a 3'-end of the chimera is modified by including a 2',3' dideoxynucleotide as the 3'-terminal nucleotide. In another preferred embodiment, the 5'-end of the chimera is modified by including a 5'—5' linkage, a 2'-5' linkage, or a label, preferably a fluorescent dye or biotin.

Generally, nucleic acid analogs are synthesized using known synthetic techniques. Detailed descriptions of the chemistry used to form polynucleotides are provided by Beaucage, 1992. The phosphoramidite method of polynucleotide synthesis for making the chimeras of the invention is a preferred method because of its efficient and rapid coupling and the stability of the starting nucleoside monomers. The synthesis is typically performed with the growing polymer chain attached to a solid support, so that excess reagents, which are in the liquid phase, can be easily removed by filtration, thereby eliminating the need for purification steps between cycles (Caruthers, 1984).

Methods of analysis and purification

High resolution and separation efficiency are challenging in the analysis and purification of high molecular weight molecules such as nucleic acid analogs, peptides, and constructs, which often adopt multiple, stable conformations due to charges and intramolecular hydrogen-bonding. For example, under the non-denaturing, reverse-phase conditions used in a conventional HPLC separation, multiple peaks may be present, complicating product identification and collection. Slab polyacrylamide gel electrophoresis (PAGE) with 7 M urea as denaturant can be used for the analysis and purification of constructs. Several odu ($A_{260nm}$, approx. 100 μg) can be isolated from an electrophoresis run by loading 10–20 crude odu on a 3 mm thick gel, performing the electrophoresis under standard conditions, excising the band after visualization under UV light against a fluorescent TLC plate (EM Science, part # 5735), soaking in water overnight at room temperature, and desalting/concentrating on an oligonucleotide purification cartridge (PE Applied Biosystems, part #400771). Anion-exchange HPLC on a polymeric adsorbent (Dionex NucleoPac PA100; 4×250 mm, Dionex Co.) can give good resolution, predictable elution patterns, and reproducible retention times. A useful protocol for constructs entails the following: mobile phase—solvent A: 100 mM NaCl, 10 mM NaOH in 10% acetonitrile (pH 12); solvent B: 800 mM NaCl, 10 mM NaOH in 10% acetonitrile (pH 12); elution flow rate=1.0 Ml/min; and a linear gradient from 0% B at 0 min to 80% B at 25 min (Andrus, 1998).

II. STRUCTURE AND SYNTHESIS OF PEPTIDES

Peptides in the cell penetrating constructs of the present invention include the third helix of the Antennapedia homeodomain, pAntp (43–58), described by Derossi, 1994, and transportan, described by Pooga, (FASEB) 1998. Both peptides may be synthesized by the methods described in Example 4, and conjugated to PNA and other nucleic acid analogs by the method of Example 6. Both peptides, and their homologs and constructive variants, are effectively internalized by several cell lines and their intracellular distribution has been characterized. The peptides, and conservative variants thereof, are preferred and shown below:

```
Transportan:    GWTLNSAGYLLGKINLKALAALAKKIL-amide    (SEQ. ID NO. 3)

pAntp(43-58):   RQIKIWFQNRRMKWKK-amide               (SEQ. ID NO. 4)
```

Transportan (galparan) is a 27 amino acid peptide from the N-terminus of the neuropeptide galanin (Bartfai, 1993; Habert-Ortoli, 1994), and mastoparan in the C-terminus, both fragments connected via a lysine. Transportan is a cell-penetrating peptide as judged by indirect immunofluorescence using the biotinylated analog, Nε13-biotinyl-transportan. The uptake of transportan is rapid and efficient in all tested cell lines. The internalization of biotinyl-transportan is energy independent and efficiently takes place from 0–37° C. and the maximal intracellular contraction is reached in about 20 min at 37° C. The cell-penetrating ability of transportan is not restricted by cell type, but is a general feature of the peptide sequence.

In the Antennapedia fragment, the presence of one or two tryptophan residues is preferred to promote internalization. Transportan contains two residues, $Trp^2$ and $Tyr^9$, that can induce inverted micelle formation. Transportan is a useful peptide vector for the introduction of different macromolecules, including hydrophobic or hydrophilic nucleic acid analogs. The internalization of transportan is receptor/protein independent and at moderate concentrations does not affect the growth of cells in culture. The energy independent cell penetration properties of transportan impart important and unexpected results when conjugated to a nucleic acid analog for sequence-specific hybridization to intracellular polynucleotides, such as nuclear DNA or mRNA.

III. CONJUGATION OF PEPTIDES AND NUCLEIC ACID ANALOGS

The general conjugation strategy to prepare a construct is to synthesize the nucleic acid analog and the peptide moieties separately. Reagents and automated synthesizers are commercially available for the synthesis of peptides and many nucleic acid analogs. Each moiety can be further derivatized to contain reactive functionality to form a linkage. Nucleic acid analogs can be covalently coupled to peptides through any suitable bond. Preferred bonds include labile bonds, such as a disulfide. To form a disulfide bond in a construct between the nucleic acid analog and peptide, the two moieties may be derivatized to bear thiol groups, one of which can bear a leaving group.

In the scheme for conjugation, or coupling, of the nucleic acid analog and the peptide moieties shown below and in Example 5, a peptide is derivatized with a nitropyridyl-leaving group (Npys) on a cysteine amino acid. The nucleic acid analog bears an unprotected cysteine thiol, and may be further derivatized with a label, such as a fluorescent dye or biotin. Nucleophilic displacement by the nucleic acid analog thiol of the Npys group of the peptide yields the disulfide-linked construct.

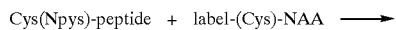

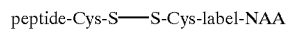

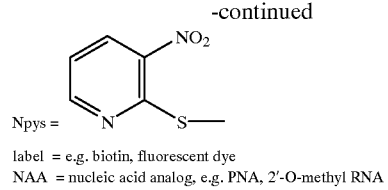

label = e.g. biotin, fluorescent dye
NAA = nucleic acid analog, e.g. PNA, 2'-O-methyl RNA

IV. INTRACELLULAR DELIVERY OF CONSTRUCTS

A utility of the present invention is intracellular delivery of hydrophilic substances e.g. peptide libraries directed against intracellular targets, cytotoxins, cytostatics, antimicrobial substances, anti viral substances, plasmids and proteins. Possible applications would include: cancer therapy, signal transduction studies (there are well known peptidergic inhibitors of G proteins, protein kinases/phosphatases etc.), the finding of new intracellular drug targets (with a library approach), transfection (or gene therapy) and studies of the results of increased intracellular protein levels (Alberts, 1989). The invention provides a powerful new tool for the study of fundamental molecular biology. The constructs and methods described herein can be used with the cells from any living species. The invention permits improved, more efficient drug discovery, aids in discerning novel points of therapeutic intervention, and provides a generalized method for the introduction of any molecule into essentially any cell subject to the membrane permeant activity of the peptide constructs of the invention.

Constructs of the invention readily enter cells (Examples 6 and 7). Cells incubated with 1 μM of certain constructs (FIG. 4), rapidly show biotinyl-PNA, detected by indirect immunofluorescence, distributed near-uniformly, including the nuclei.

Galanin is a widely distributed neuropeptide of 29 or 30 amino acids with a broad spectrum of biological effects (Pooga (FASEB), 1998; Bartfai, 1995). The galanin receptor type 1 GalR1, was first cloned from human Bowes melanoma cells and then from rat brain (Habert-Ortoli, 1994). GalR1 is highly conserved between species and is abundantly present in the hypothalamus, hippocampus and spinal cord. Examples of the antisense effect of PNA-S-S-peptide constructs (e.g. A and B) by down-regulation of the expression of GalR1 are presented here. Also presented in Example 9 is in vivo suppression of the galanin receptor in rat spinal cord and that reduced expression of galanin receptors significantly modifies the pain response. The reduced pain transmission correlates with the reduced amount of $^{125}$I-galanin binding (i.e. functional galanin receptors).

Figure 5:
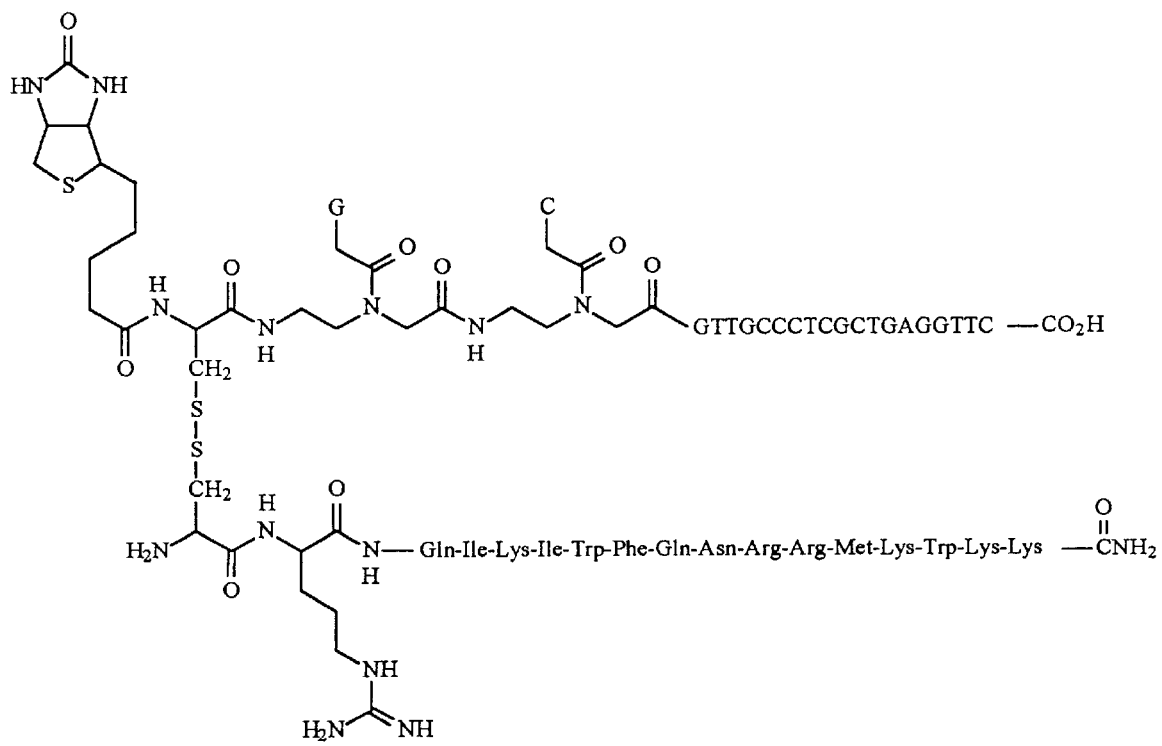
FIG. 5 shows further detail of the structure of pAntp (43–58)-S-S-(biotinyl PNA21) A.
Figure 7:
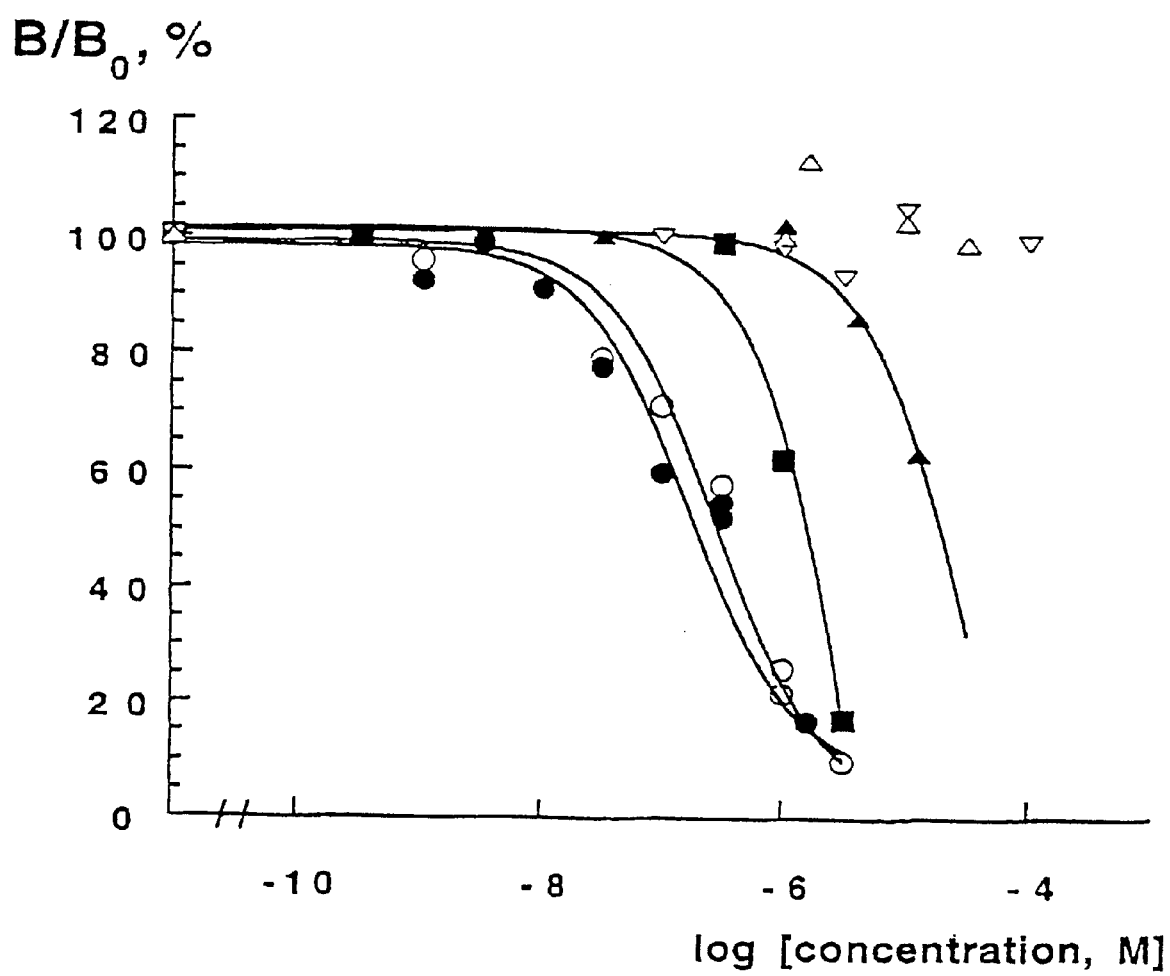

Expression of the human galanin receptor in cos-7 cells was studied by the antisense effects of PNA, native DNA oligonucleotides, and constructs A and B (FIGS. 4 and 5). The transient expression of the galanin receptors in cos-7 cells is reduced when the PNA sequence is cotransfected into the cells with the plasmid (Example 7). More pronounced inhibition of galanin receptor synthesis is achieved by pre-incubation of the plasmid with the PNA. Significantly stronger antisense effects are obtained when constructs A and B are introduced into the cells, probably due to the higher intracellular concentration obtained (FIG. 6). The decrease in the galanin receptor content is dose dependent, proportional to the concentration of constructs A and B (FIG. 7). The control constructs of A and B where scrambled, nonsense PNA is used did not have any effect on specific $^{125}$I-galanin binding.

perature for 1 hour, followed by ether precipitation of the crude PNA.

The 21mer cPNA (18–32) was synthesized with a cysteine amino acid residue at the amino terminus. The PNA sequence is in the antiparallel orientation complementary to nucleotides 18–38 of the type 1 human galanin receptor mRNA.

```
                          18                          38
HGalR1 cDNA: GTC GGG AAC CTC AGC GAG GGC AAC GC   (SEQ. ID NO. 5)

21mer  C TTG GAG TCG CTC CCG TTG CG  (SEQ. ID NO. 6)

16mer  C TTG GAG TCG CTC CCG         (SEQ. ID NO. 7)

6mer   C TTG GA                      (SEQ. ID NO. 8)
```

V. EXAMPLES

The invention will be further clarified by a consideration of the following examples, which are intended to be purely exemplary of the present invention and not to in any way limit its scope.

EXAMPLE 1
Synthesis of PNA

Automated synthesis of PNA can be performed using an Applied Biosystems Model 394 DNA/RNA synthesizer or 433A Peptide synthesizer (The Perkin-Elmer Corporation, PE Applied Biosystems Division) according to the general procedures described in the synthesizer manufacturer's Users Manual, as well as Egholm, 1993.

Synthesis of PNA can be conducted on a MBHA (methylbenzhydrylamine) linker, high-loaded polystyrene support at 2–50 μmole scale with the cycle of steps in Table 2. The cycle is conducted for each Boc-PNA monomer addition (Dueholm, 1994).

TABLE 2

PNA synthesis cycle on the Model 433 synthesizer

| Step | Function | Reagents delivered | Time |
|---|---|---|---|
| 1 | Boc removal | TFA/m-cresol, 95/5 | 6 min |
| 2 | wash | DMF/DCM, 1/1 | 2 min |
| 3 | wash | pyridine/DMF, 5195 | 2 min |
| 4 | coupling | 5 equiv. Boc-PNA monomer (0.05 M), 4.5 equiv. HATU, DIEA | 15 min |
| 5 | wash | DMF/DCM, 1/1 | 2 min |
| 6 | capping | acetic anhydride/DMF, 5/95 | 5 min |
| 7 | wash | DMF/DCM, 1/1 | 2 min |
| 8 | wash | piperidine/DMF, 1/1 | 2 min |
| 9 | wash | DMF/DCM, 1/1 | 2 min |

DIPEA  diisopropylethylamine
TFA    trifluoroacetic acid
HATU   1-hydroxy-7-azabenzotriazole-tetramethyluronium hexafluorophosphate
DCM    dichloromethane
DMF    dimethylformamide The synthesis of PNA is performed with standard synthesis techniques and nucleobase $A^{bz}$, $C^{bz}$, $G^{ibu}$, T) and primary amino (MMT, Fmoc or Boc) protecting groups. However, the nitropyridyl sulfide protecting group (Npys) for cysteine is cleaved with piperidine which mandates the MMT or Boc methods if NPys is included in the sequence. At the 5 μmole scale, a 3 ml reaction vessel is used, with a total reaction volume of 440 μl. At the end of synthesis, the PNA is cleaved with TFMSA (trifluoromethanesulfonic acid) at room tem-

EXAMPLE 2
Synthesis of PNA/DNA chimera

Automated synthesis of PNA/DNA chimera can be performed using an Applied Biosystems Model 394 DNA/RNA synthesizer or 433A Peptide synthesizer (The Perkin-Elmer Corporation, PE Applied Biosystems Division) according to the general procedures described in the users manual as well as Uhlmann, 1996; Van der Laan, 1997 and Vinayak, 1997.

The support used for PNA/DNA chimera synthesis is a non-swelling, high-cross linked polystyrene bead with a hydroxymethylbenzoic acid linker (Vinayak, 1997). PNA monomers for chimera synthesis use the monomethoxytrityl (MMT) group for primary amino protection. In the first step, the monomer, HATU and DIPEA, each dissolved in DMF/acetonitrile, 1/1, are delivered concurrently to the reaction cartridge. After 16 min, capping reagents are delivered. To minimize the tendency of the primary amino function of PNA to migrate or cyclize, the 5'(N) end of the PNA and PNA-DNA chimera is acetylated after removal of the final MMT group. Reagents necessary to link the DNA and PNA moieties, and other procedures for chimera synthesis, cleavage, deprotection, and purification are described by Van der Laan, 1997. In this approach, the chimera can be made as one molecule, in a single cartridge and a single synthesizer.

After synthesis, the chimera are cleaved from the support using ammonium hydroxide (1.5 mL) or a mixture of MeOH:t-BuNH$_2$:H$_2$O (1:1:2) and the exocyclic amine protecting groups are removed by heating the solution at 55 to 85° C. for 1 to 16 h. The solution is then concentrated to ½ the original volume, water (1 mL) is added and the chimera is desalted by gel-filtration (Sephadex™, Pharmacia). The chimeras can be analyzed and purified by reverse phase HPLC, anion-exchange HPLC, capillary gel electrophoresis, polyacrylamide gel electrophoresis, and other conventional techniques (Andrus, 1992).

EXAMPLE 3
Synthesis of a 5'-amino, 2'-O-methyl RNA oligonucleotide

Automated synthesis of 5'-amino, 2'-O-methyl RNA oligonucleotide can be performed using an Applied Biosystems Model 394 DNA/RNA synthesizer (The Perkin-Elmer Corporation, PE Applied Biosystems Division) according to the general procedures described in the users manual as well as Sproat, 1994. The oligonucleotides are synthesized with DNA (dA$^{bz}$, dG$^{dmf}$, dC$^{bz}$, T) and 2'-O-Me RNA (A$^{bz}$, G$^{dmf}$, C$^{bz}$, U) phosphoramidite nucleoside monomers. The eight monomers are auto-diluted with dry acetonitrile (<50 ppm H$_2$O) and have useful lifetimes on the synthesizer of 2–3 weeks. For each cycle at the 0.2 μmole scale, 40 μl of 0.1 M phosphoramidite nucleoside (ca. 3.5 mg) in acetonitrile is delivered concurrently with 120 μl of 0.5 M 5-H tetrazole in acetonitrile for coupling. Synthesis and cleavage from the solid support are automated without interruption, utilizing all 8 monomer positions and specific 25 second (DNA) and 4 minute (2'-OMe RNA) coupling times. The 5' amino group is coupled to the support-bound oligonucleotide, with N-trifluoroacetyl, 6-aminohexyl, cyanoethyldiisopropylaminophosphoramidite as the last monomer. Synthesis efficiency is measured in real-time with a trityl conductivity monitor and generally exhibits >98% average stepwise yield. High-cross link, 1000 Å pore diameter polystyrene, loaded at 12 μmole 3' nucleoside/gm support, is used to generate about 40 crude odu of oligonucleotide at the 0.2 μmole scale (ca. 1.6 mg). Scale-up to 1 μmole gives 200 crude odu (ca. 8 mg) with 1000 Å, 3' nucleoside CPG support. The nucleobase protecting groups for A, G, and C are selected for comparable deprotection rates in concentrated ammonium hydroxide (1 hour at 65° C.). After cleavage, deprotection, and purification by HPLC, 5'-amino, 2'-O-methyl RNA oligonucleotides up to 50 bases in length can be routinely attained in high purity and yield.

EXAMPLE 4
Synthesis of biotin-transportan peptide

The peptides and PNA oligomers are assembled on ABI 431A and 433 Peptide synthesizers (PE Applied Biosystems, Foster City, Calif.) using the T-BOC reagent strategy of solid-phase synthesis (Geiser, 1988).

Peptides were synthesized in a stepwise manner of amino acid addition at the 0.1 mmol scale on MBHA-polystyrene support (1.1 mmol amino/g loading, Bachem, Switzerland) to obtain C-terminal amide peptides. Activation of amino acid monomers was conducted using dicyclohexylcarbodiimide (DCC)/hydroxybenzotriazole (HOBT). Deprotection of formyl and benzyl groups from side chains was carried out using the TFMSA (trifluoromethanesulfonic acid). The DNP protecting groups on histidine can be removed with 20% (v/v) thiophenol/DMF at room temperature for 1 h. For the synthesis of biotin-transportan, $N^{\epsilon 13}$Fmoc-transportan-MBHA resin was employed. The N-Fmoc protecting groups were removed with 20% piperidine in DMF. Biotin was coupled to the peptide manually by adding a 3× excess of HOBT and DCC-activated biotin in DMF to the peptide-resin. The coupling reaction was complete after 1 h at room temperature. The peptides were finally cleaved from the resin with liquid HF at 0° C. for 30 min. Purity of the peptides was assessed as >99% after reverse-phase HPLC purification, by HPLC analysis on Nucleosil 120-3 C18 column (0.4×10 cm). Identity was verified by molecular mass determination on a Plasma Desorption Mass Spectrometer (BioIon 20, Applied Biosystems).

EXAMPLE 5
Conjugation of peptide and PNA

Figure 3:
FIG. 3 illustrates an example of conjugation of a nucleic acid analog, human galanin receptor biotin-Cys-cPNA 15mer 1 to a peptide, Cys(Npys)-pAntp(43–58) 2, to form the construct cPNA(18–32)-S-S-pAntp(43–58).

A 15mer PNA $H_2N$-CCC TCG CTG AGG TCC-amide (SEQ. ID NO. 9) is designed as an antisense sequence against human galanin receptor mRNA and synthesized. The PNA was coupled at the N-terminus to a cysteine amino acid. In order to enable the detection of the intracellular localization of the construct in the cell, the amino portion of the cysteine was biotinylated to give biotin-cys-CCC TCG CTG AGG TCC-amide. Transporter peptide pAntp(43–58), a 16 amino acid third helix peptide of the homeodomain of Antennapedia pAntp (43–58), which is known to translocate through biological membranes (Derossi, 1996), was synthesized as 2 to contain a nitropyridylsulfide cysteine residue at the N terminus. Purified Cys(NPys)-peptide 2 was mixed with Cys-PNA 1 in a 1:1 molar ratio (or with a slight excess of PNA) in degassed 40% dimethylformamide in DMSO. A disulfide bridge was formed between the cysteine of the PNA and the cysteine of peptide to give the construct, cPNA (18–32)-S-S-pAntp(43–58), isolated in a pure state after HPLC purification (FIG. 3). to give disulfide linked construct, e.g. A (FIGS. 3 and 5). The concentration of reagents should be as high as possible, e.g. 0.02–0.10 mM. The reaction was allowed to proceed with gentle rocking under nitrogen and exclusion of light for 18–24 h. The crude product was purified by reverse-phase HPLC. Identity was verified by molecular mass spectroscopy as in Example 4.

EXAMPLE 6
Infusion of cells with constructs

Human melanoma cells Bowes' (ATCC CRL-9607) were cultivated in Eagle's Minimal Essential Medikum (MEM) ("Gibco"), supplemented with 10% fetal calf serum, 2 mM glutamine, 100 U/ml penicillin and 100 μg/ml streptomycin. The cells were grown to about 50% confluence in the microchambers on the preparate glass. Constructs and controls (PNA and peptides) were added directly into the cell medium and incubated in 5% $CO_2$ at 37° C. for specified time periods. Cells on glass were rinsed briefly with PBS and fixed with a mixture of 4% paraformaldehyde and 1% glutaric aldehyde in PBS. Fixed cells were permeabilized in methanol for 10 min at −20° C. and sites for nonspecific binding blocked with 5% BSA in PBS. Internalized biotinylated PNA and peptides were detected with streptavidin-FITC (Amersham, 1:100 diluted) or avidin-TRITC (Sigma, 1:200 diluted).

When human Bowes' melanoma cells are incubated with 1 μM of either construct A or B (FIG. 4) for 4 h at 37° C., the biotinyl-PNA is detected in every cell and distributed near-uniformly including the nuclei, by indirect immunofluorescence. The staining pattern is similar if not identical for both transport peptides used, even though the peptides themselves, pAntp(43–58) and transportan, show different preferences in intracellular localization. Transportan predominantly resides in the membranous structures while pAntp(43–58) shows a preference for the nucleus. PNA is cleaved from the peptide, since the staining patterns of the constructs and the peptides-alone are different. Within cells, the labile disulfide bond of the constructs A and B which connects the peptide to the PNA is likely to be cleaved quickly, leading to a dissociation of the PNA from the peptide, thereby permitting association with the target mRNA in the cytosol or translocation into the nucleus. The three constructs with PNA of lengths 6, 16, and 21 units long are delivered into the cells with similar efficiencies (Example 1).

EXAMPLE 7
Incubation of cos-7 cells with PNA only

Cos-7 cells were cotransfected by electroporation with 2 μg of galanin receptor carrying pRK8 plasmid and 2 μg of $cPNA_{21}$ and 50 μg salmon sperm DNA as carrier into $5 \times 10^6$ cells. For comparison, identical transfections were performed without PNA and with the carrier DNA only. The transfected cells were grown for 48 h and the amount of the expressed galanin receptors was estimated by the binding of $^{125}$I-galanin.

Cells were lysed by suspending them in hypotonic ice-cold 5 mM HEPES buffer containing 2.5 mM $MgCl_2$, 0.5 mM EDTA (pH 7.3) and subsequently incubated for 10 min on ice. The resulting microsomal membrane fraction was collected by centrifugation at 10,000× g for 10 min at 4° C.

and weighed. The membranes were resuspended in HEPES buffered Krebs-Ringer (HKR) solution, supplemented with 0.05% (w/v) bovine serum albumin and 0.1% (w/v) bacitracin and homogenized with a glass-Teflon homogenizer. The equilibrium binding experiments were performed in a final volume of 300 µl HKR containing 200 pM [$^{125}$I]-galanin (NEN), cell membranes and galanin. Samples were incubated for 30 min at 37° C. in a shaking water bath. The incubation was terminated by the addition of 2×10 ml ice-coled HKR, followed by the rapid filtration over Whatman GF/C glass fibre filters precoated for 2–3 h in 0.3% (v/v) polyethyleneimine solution. The radioactivity retained on the filters was determined in a gamma counter (Packard). The specific binding was determined as the part of total binding that could be displaced with large excess of unlabelled galanin (1 µM. Protein concentration was determined according to Peterson, 1977.

EXAMPLE 8
Down-regulation of human galanin receptor type 1 in Bowes cell line A variety of constructs and control nucleic acid analogs were delivered to Bowes melanoma cells (FIG. 6) to demonstrate the antisense effects of the PNA constructs in the down-regulation of translation of human galanin receptor. Strong inhibitory effects on $^{125}$I-galanin binding are obtained when the human cPNA sequence is the nucleic acid analog moiety of constructs with transportan and pAntp. The maximal decrease in specific binding of $^{125}$I-galanin is seen with constructs targeting nucleotides 18–38 in the coding region of galanin receptor type 1 mRNA. Treatment of Bowes cells with 3 µM of cPNA h(18–38)-S-S-pAntp A or 1.5 µM of cPNA h(18–38)-S-S-transportan B leads to 91% and 83% decrease in binding, respectively (FIG. 6). The maximal decrease, by 91% (3 µM A) or 83% (1.5 µM B), in specific binding of $^{125}$I-galanin by galanin receptors was detected after a 36 h incubation at 37° C. of the cells with constructs A and B. PNA only, complementary to the translation start site of GalR1 mRNA, targeting nucleotides 1–21, is less potent. Predictions of RNA secondary structure show that regions 1–21 and 18–38 of the coding region of the galanin receptor type 1 mRNA mainly exist in unpaired loop structures, confirming the possibility to efficiently target respective regions with PNA.

Human and rat GalR1 are highly homologous, however the mRNAs in positions 1–21 and 18–38 differ by 6 and 5 nucleotides, respectively. The possibility for the interaction of rat specific PNA with mRNA for human galanin receptor may explain some low antisense effects of respective constructs. Incubation with 1 µM cPNA r(1–21)-S-S-pAntp and cPNA r(18–38)-S-S-pAntp (A) leads to 13% and 18% reduction in specific binding of $^{125}$I-galanin to galanin receptors after 36 h.

As a comparison, the effect of an unmodified phosphodiester antsense 21mer oligonucleotide complementary to region 18–38 was measured. At oligonucleotide concentration of 10 µM, only 5% reduction in $^{125}$I-galanin binding was observed (FIG. 6), due to the relatively low nuclease stability of phosphodiester DNA. A phosphorothioate 21mer complementary to nucleotides 18–38 of human GalR1 mRNA shows pronounced antisense effect, although at significantly higher concentration than corresponding PNA. Incubation with 12 µM phosphorothioate h(18–38) for 36 h results in a 37% decrease in galanin binding.

Western blot analysis shows a decrease in specific binding of $^{125}$I-galanin to galanin receptors after treatment with PNA-S-S-peptide constructs, e.g. A and B, is accompanied by a decrease of galanin receptor protein content in cellular membranes (results not shown), demonstrating the correlation between attenuation of protein expression and $^{125}$I-galanin binding.

EXAMPLE 9
Down-regulation of rat galanin receptor type 1 in rat spinal cord in vivo Construct A and the corresponding scrambled 21mer PNA containing construct were administered intrathecally at 150 µM through chronically implanted catheters in rats. Three injection were given during a period of 36 h and acute electrophysiological experiments were conducted approximately 12 h after the last injection.

No signs of toxicity, paralysis, or motor impairment was observed in any case. The nociceptive flexor reflex was recorded as EMG from the ipsilateral hamstring muscles in response to high threshold electrical stimulation. The effects of the administration of galanin on the baseline flexor reflex and on the facilitation of the reflex induced by repetitive C-fibre stimulation were evaluated and compared between rats receiving construct A and scramble sequence (FIG. 8). Conditioning stimulation (CS) of C-fibres elicits a brief facilitation of the flexor reflex similarly in rats receiving the constructs with 21 mer cPNA or the constructs with scrambled PNA sequence. Injected galanin inhibits doesdependently the reflex facilitation by C-fibre CS in the case of untreated rats and those treated with the constructs with scramble 21mer PNA. This effect of galanin is reduced approximately 100 fold in rats receiving construct A (FIG. 8).

These results clearly show that constructs such as A shift the dose-response curve for the blocking effect of intrathecal galanin on the C-fibre CS-induced increase in spinal cord excitability 100-fold, implying a profound down-regulation of the type 1 galanin receptors, which appear to mediate the inhibitory effect of galanin.

EXAMPLE 10
Control down-regulation of galanin-receptor with DNA phosphodiester oligonucleotides RINm5F cells As a comparison, three different antisense phosphodiester oligonucleotides were formulated with the polyamine surfactant, LIPOFECTAMINE™ and transfected into galanin receptor-containing RINm5F cells. RINm5F insulinoma cells were grown in RPMI 1640 medium supplemented with 5% (v/v) fetal bovine serum, 2 mM L-glutamine, 100 IU/ml penicillin and 100 µg/ml streptomycin in 5% $CO_2$-enriched air at 37° C. At the time of addition of oligodeoxynucleotides, serum and antibiotics-free Optim-MEM® 1 reduced serum medium was used. All cell culture mediums were purchased from GIBCO.

The sequences of the oligonucleotides were complementary to the region following the ATG codon of the rat type 1 galanin receptor:

```
                                  (SEQ. ID NO. 10)
5' CAC CGC AGC CAG TTC CAT 3' bases 1–18

(SEQ. ID NO. 11)
5' GGT CGC TCC CAT TCC CTT 3' bases 15–32

(SEQ. ID NO. 12)
5' GGT CGC TCC CAT TCC CCT 3' bases 29–46
```

Final concentrations ranging from 0.2 to 20 µM were tested in incubations of different lengths (4–24 h) followed by 24 h growth in drug-free medium and subsequent harvest and $^{125}$I-galanin binding experiment. No effect of these oligonucleotides on the level of expression of receptor protein could be demonstrated under any condition. The lack of effect could be explained by the relatively low stability of the phosphodiester oligonucleotides due to nuclease degradation. Alternatively, the galanin receptors in the RINm5F cells may be a different subtype. Nonetheless, these negative results in RINm5F cells clearly demonstrate the necessity of aspects of the present invention; a stable nucleic acid analog for targetting intracellular polynucleotides and cell-penetrating transport peptides.

All publications and patent applications are herein incorporated by reference to the same extent as if each individual publication or patent application was specifically and individually indicated to be incorporated by reference.

Although only a few embodiments have been described in detail above, those having ordinary skill in the molecular biology art will clearly understand that many modifications are possible in the preferred embodiment without departing from the teachings thereof. All such modifications are intended to be encompassed within the following claims.

We claim:

1. A membrane-permeable construct for transport across a lipid membrane comprising:

a nucleic acid analog which hybridizes with an intracellular polynucleotide;

a peptide comprising $R_1$-INLKALAALAKKIL-$R_2$    (SEQ ID NO: 1)

wherein each of $R_1$ and $R_2$ is a peptide, an amino acid, $NH_2$, H, or OH, at least one of $R_1$ and $R_2$ is a peptide, and said nucleic acid analog is bonded to the one of $R_1$ and $R_2$ that is a peptide; and a labile bond linking the nucleic acid analog and the peptide.

2. The construct of claim 1 comprising the sequence

GWTLNSAGYLLGKINLKALAALAKKIL    (SEQ. ID NO. 3);

including homologs and conservative variants thereof.

3. The construct of claim 1 wherein the nucleic acid analog is a PNA or PNA/DNA chimera.

4. The construct of claim 1 wherein the nucleic acid analog is a 2'-O-alkyl RNA or 2'-O-alkyl RNA/DNA chimera.

5. The construct of claim 1 wherein the nucleic acid analog is a nucleobase-modified oligonucleotide.

6. The construct of claim 1 wherein the peptide and the nucleic acid analog are conjugated by a bond which is cleaved after transport into a cell.

7. The construct of claim 6 wherein the bond is a disulfide bond.

8. The construct of claim 6 wherein the bond is an ester bond.

9. The construct of claim 1 further comprising a label.

10. The construct of claim 9 wherein the label is selected from the group consisting of biotin, dinitrophenyl, acridine, fluorescein, rhodamine, cyanine, digoxigenin, intercalator, minor-groove binder and chemiluminescent precursor having the structure

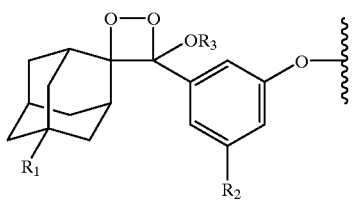

where $R_1$ is hydrogen or halogen; $R_2$ is phosphate, galactoside, glucoside, glucuronide, trialkylsilyloxy, acyloxy, or hydrogen; and $R_3$ is methyl, ethyl, and lower alkyl.

11. The construct of claim 1 wherein one of $R_1$ and $R_2$ comprises cysteine and said nucleic acid analog is disulfide bonded to said cysteine.

12. The construct of claim 1 comprising the structure

where $R_1$ is a peptide and NAA is the nucleic acid analog.

13. The construct of claim 12 wherein NAA is a PNA or PNA/DNA chimera joined to K through a disulfide bond.

14. The construct of claim 12 wherein $R_1$ comprises

GWT or GWTLNSAGYLLG.    (SEQ. ID NO. 2)

15. The construct of claim 12 wherein the C-terminal L is amidated.

16. The construct of claim 12 wherein the disulfide bond is disposed between a pair of cysteine residues.

17. A method of selectively inhibiting DNA transcription, RNA translation, RNA or DNA expression, DNA replication, or DNA or RNA regulatory function of a preselected one or a subset of DNA or RNA sequences in a living cell, the method comprising the steps of:

providing a membrane-permeable construct of claim 1 for transport across a lipid membrane; and exposing a cell to the construct so that the construct is transported across, and permeates at least, the outer membrane of the cell, and the PNA hybridizes with a intracellular polynucleotide disposed therein.

18. The method of claim 17 wherein the construct comprises a label.

19. The method of claim 18 wherein the label is a fluorescent label.

20. The method claim 19 further comprising the step of detecting the fluorescent label after the construct is transported into the cell, and before or after the labile bond is cleaved.

21. The method of claim 18 wherein the label is a biotin label.

22. The method claim 21 further comprising the step of detecting the biotin label after the construct is transported into the cell, and before or after the labile bond is cleaved.

* * * * *